(12) United States Patent
Lin et al.

(10) Patent No.: US 11,318,170 B2
(45) Date of Patent: May 3, 2022

(54) TREATMENT OF BRAIN DAMAGE USING UMBILICAL CORD BLOOD CELLS

(75) Inventors: Shinn-Zong Lin, Hualien (TW); Woei-Cherng Shyu, Taipei (TW); Hung Li, Taipei (TW)

(73) Assignee: StemCyte, Inc., Baldwin Park, CA (US)

( * ) Notice: Subject to any disclaimer, the term of this patent is extended or adjusted under 35 U.S.C. 154(b) by 494 days.

(21) Appl. No.: 12/935,077

(22) PCT Filed: Mar. 26, 2009

(86) PCT No.: PCT/US2009/001915
§ 371 (c)(1),
(2), (4) Date: May 19, 2011

(87) PCT Pub. No.: WO2009/120368
PCT Pub. Date: Oct. 1, 2009

(65) Prior Publication Data
US 2011/0256107 A1    Oct. 20, 2011

Related U.S. Application Data

(60) Provisional application No. 61/072,173, filed on Mar. 28, 2008.

(51) Int. Cl.
*A61K 35/51* (2015.01)
*A61K 9/00* (2006.01)

(52) U.S. Cl.
CPC ............ *A61K 35/51* (2013.01); *A61K 9/0085* (2013.01)

(58) Field of Classification Search
None
See application file for complete search history.

(56) References Cited

U.S. PATENT DOCUMENTS

| 4,714,680 | A | 12/1987 | Civin |
| 4,965,204 | A | 10/1990 | Civin |
| 5,035,994 | A | 7/1991 | Civin |
| 5,061,620 | A | 10/1991 | Tsukamoto et al. |
| 5,087,570 | A | 2/1992 | Weissman et al. |
| 7,427,597 | B2 | 9/2008 | Li et al. |
| 2001/0038836 | A1* | 11/2001 | During et al. ............... 424/93.7 |
| 2006/0233765 | A1 | 10/2006 | Messina et al. |
| 2006/0263332 | A1 | 11/2006 | Li et al. |
| 2006/0264365 | A1 | 11/2006 | Li et al. |

(Continued)

FOREIGN PATENT DOCUMENTS

| WO | WO 2005/003333 A2 | 1/2005 |
| WO | WO 2005/112959 A2 | 12/2005 |
| WO | WO 2007/039150 A2 | 4/2007 |

OTHER PUBLICATIONS

Vendrame et al, Infusion of Human Umbilical Cord Blood Cells in a Rat Model of Stroke Dose-Dependently Rescues Behavioral Deficits and Reduces Infarct Volume, 2004, Stroke 35: 2390-2395.*

(Continued)

*Primary Examiner* — Sharmila G Landau
*Assistant Examiner* — Stephanie A McNeil
(74) *Attorney, Agent, or Firm* — Wolf, Greenfield & Sacks, P.C.

(57) ABSTRACT

The invention relates to the treatment of chronic stroke, traumatic brain injury, and neurodegenerative disorders using umbilical cord blood cells.

23 Claims, 13 Drawing Sheets

(56) References Cited

U.S. PATENT DOCUMENTS

| | | |
|---|---|---|
| 2006/0275271 A1 | 12/2006 | Chow |
| 2007/0116677 A1 | 5/2007 | Li et al. |
| 2007/0141035 A1 | 6/2007 | Li et al. |
| 2007/0237751 A1 | 10/2007 | Sanberg et al. |
| 2008/0166324 A9 | 7/2008 | Chow |
| 2010/0310530 A1 | 12/2010 | Lin et al. |

OTHER PUBLICATIONS

Feigin et al, Stroke epidemiology: a review of populationbased studies of incidence, prevalence, and case-fatality in the late 20th century, 2003, The Lancet Neurology 2: 43-54.*

Takahashi et al, Differentiation of Chronic Lesions after Stroke in stroke-Prone Spontaneously Hypertensive Rats Using Diffusion Weighted MRI, 1993, MRM 30:485-488.*

Kim et al, Motor Function Recovery after adipose Tissue Derived Mesenchymal Stem Cell Therapy in Rats with Cerebral Infarction, 2006, J Korean Neurosurg Soc 40 : 267-272.*

Dawson et al, Taming the clot-buster tPA, 2006, Nature Medicine 12(9): 993-994 (Year: 2006).*

Hao et al., Studies on the dynamics of biological characteristics of CD133+ cells from human umbilical cord blood during short-term culture. Journal of Experimental Hematology. Dec. 2003;11(6):569-75. Chinese.

Chen et a., Resuscitation from experimental heatstroke by transplantation of human umbilical cord blood cells. Crit Care Med. Jun. 2005;33(6):1377-83.

Kekarainen et al., Optimization of immunomagnetic separation for cord blood-derived hematopoietic stem cells. BMC Cell Biol. Aug. 1, 2006;7:30.

Lin, Miraculous Umbilical Cord Blood—Omnipotent Stem Cells. Department of Pediatrics, National Taiwan University Hospital. Mar. 17, 2003. 3 pages.

Pomye et al., Different expression of angiogenic genes in CD133+/CD34+ cell fraction derived from cord blood and adult bone marrow. Experimental Hematology. 2003;31(7):209. Abstract # 445.

Suzuki et al., Development of a highly efficient ex vivo expansion system of human hematopoietic stem cells using delta1-FC chimeric protein. Artificial Blood. 2007;14(4):108-12.

Tsuji, Capability of cord blood hematopoietic stem cells: a comparison with adult bone marrow hematopoietic stem cells. Inflammation and Regeneration. 2003;23(3):181-5.

Dong et al., Molecular mechanisms of excitotoxicity and their relevance to pathogenesis of neurodegenerative diseases. Acta Pharmacol Sin. Apr. 2009;30(4):379-87. doi: 10.1038/aps.2009.24.

Hacke et al., Association of outcome with early stroke treatment: pooled analysis of ATLANTIS, ECASS, and NINDS rt-PA stroke trials. Lancet. Mar. 6, 2004;363(9411):768-74.

Monville et al., Comparison of incremental and accelerating protocols of the rotarod test for the assessment of motor deficits in the 6-OHDA model. J Neurosci Methods. Dec. 15, 2006;158(2):219-23. Epub Jul. 11, 2006.

Pavelko et al., Acceleration in the rate of CNS remyelination in lysolecithin-induced demyelination. J Neurosci. Apr. 1, 1998;18(7):2498-505.

Ramirez et al., Umbilical Cord Stem Cell Therapy for Cerebral Palsy. Med Hypotheses Res. Apr. 2006;3(2):679-86.

Liu et al., Axonal sprouting into the denervated spinal cord and synaptic and postsynaptic protein expression in the spinal cord after transplantation of bone marrow stromal cell in stroke rats. Brain Res. May 29, 2007;1149:172-80. Epub Feb. 27, 2007.

Sicard et al., Review: Animal models of focal brain ischemia. Experimental & Transl. Stroke Med. 2009, 1:7; 1-6. Published Jul. 16, 2009.

[No Author Listed] Umbilical Cord Blood Injections Aid Aging Brains. Mar. 17, 2008. Last accessed Mar. 18, 2008 at http://http.www.washingtonpost.com/wp-dyn/content/article/2008/03/17/AR2008031701487_p . . . 1 page.

Borlongan et al., Central nervous system entry of peripherally injected umbilical cord blood cells is not required for neuroprotection in stroke. Stroke. Oct. 2004;35(10):2385-9. Epub Sep. 2, 2004.

Borlongan et al., Early assessment of motor dysfunctions aids in successful occlusion of the middle cerebral artery. Neuroreport. Nov. 16, 1998;9(16):3615-21. Abstract only.

Borlongan et al., Viability and survival of hNT neurons determine degree of functional recovery in grafted ischemic rats. Neuroreport. Aug. 24, 1998;9(12):2837-42. Abstract only.

Chang et al., Intravenous administration of bone morphogenetic protein-7 after ischemia improves motor function in stroke rats. Stroke. Feb. 2003;34(2):558-64.

Chen et al., Resuscitation from experimental heatstroke by transplantation of human umbilical cord blood cells. Crit Care Med. Jun. 2005;33(6):1377-83. Abstract only.

Chen et al., Human umbilical cord blood-derived CD34+ cells cause attenuation of multiorgan dysfunction during experimental heatstroke. Shock. Jun. 2007;27(6):663-71.

Chen et al., Intravenous administration of human umbilical cord blood reduces behavioral deficits after stroke in rats. Stroke. Nov. 2001;32(11):2682-8.

Dunnett et al., A lateralised grip strength test to evaluate unilateral nigrostriatal lesions in rats. Neurosci Lett. Apr. 17, 1998;246(1):1-4. Abstract only.

Gloster et al., The T alpha 1 alpha-tubulin promoter specifies gene expression as a function of neuronal growth and regeneration in transgenic mice. J Neurosci. Dec. 1994;14(12):7319-30.

Gregory et al., Dkk-1-derived synthetic peptides and lithium chloride for the control and recovery of adult stem cells from bone marrow. J Biol Chem. Jan. 21, 2005;280(3):2309-23. Epub Oct. 25, 2004.

Gregory et al., The Wnt signaling inhibitor dickkopf-1 is required for reentry into the cell cycle of human adult stem cells from bone marrow. J Biol Chem. Jul. 25, 2003;278(30):28067-78. Epub May 9, 2003.

Ha et al., Neural phenotype expression of cultured human cord blood cells in vitro. Neuroreport. Nov. 16, 2001;12(16):3523-7. Abstract only.

Hwang et al., Human umbilical cord blood-derived CD34+ cells can be used as a prophylactic agent for experimental heatstroke. J Pharmacol Sci. Jan. 2008;106(1):46-55. Epub Jan. 11, 2008.

Kobari et al., CD133+ cell selection is an alternative to CD34+ cell selection for ex vivo expansion of hematopoietic stem cells. J Hematother Stem Cell Res. Apr. 2001;10(2):273-81. Abstract only.

Li et al., Human marrow stromal cell therapy for stroke in rat: neurotrophins and functional recovery. Neurology. Aug. 27, 2002;59(4):514-23. Abstract only.

Lin et al., CD34+ Stem Cell Therapy in Chronic Stroke Patients. Cell Transplantation. 2008;17(4):472.

Lin et al., CD34+ Stem Cell Therapy in Chronic Stroke Patients. Center for Neuropsychiatry, China Medical University Hospital. TaiChung, Taiwan. Integrating Discovery and Innovation into Practice. San Diego, California. Sep. 15-20, 2007. Poster 5 pages.

Lu et al., Intravenous administration of human umbilical cord blood reduces neurological deficit in the rat after traumatic brain injury. Cell Transplant. 2002;11(3):275-81.

Munoz et al., Human stem/progenitor cells from bone marrow promote neurogenesis of endogenous neural stem cells in the hippocampus of mice. Proc Natl Acad Sci U S A. Dec. 13, 2005;102(50):18171-6. Epub Dec. 5, 2005. Erratum in: Proc Natl Acad Sci U S A. Feb. 7, 2006;103(6):2000-2.

Nan et al., Infusion of human umbilical cord blood ameliorates neurologic deficits in rats with hemorrhagic brain injury. Ann N Y Acad Sci. May 2005;1049:84-96. Abstract only.

Newman et al., Cytokines produced by cultured human umbilical cord blood (HUCB) cells: implications for brain repair. Exp Neurol. May 2006;199(1):201-8. Epub May 30, 2006.

Okamoto et al., Common molecular pathways involved in human CD133+/CD34+ progenitor cell expansion and cancer. Cancer Cell Int. Jun. 8, 2007;7:11. 12 pages.

Ross et al., Spatiotemporal expression of angiogenesis growth factor receptors during the revascularization of regenerating rat liver. Hepatology. Dec. 2001;34(6):1135-48.

(56) References Cited

OTHER PUBLICATIONS

Saporta et al., Human umbilical cord blood stem cells infusion in spinal cord injury: engraftment and beneficial influence on behavior. J Hematother Stem Cell Res. Jun. 2003;12(3):271-8. Abstract only.

Shyu et al., Functional recovery of stroke rats induced by granulocyte colony-stimulating factor-stimulated stem cells. Circulation. Sep. 28, 2004;110(13):1847-54. Epub Sep. 20, 2004.

Shyu et al., Granulocyte colony-stimulating factor for acute ischemic stroke: a randomized controlled trial. CMAJ. Mar. 28, 2006; 174(7):927-33. Epub Mar. 3, 2006.

Shyu et al., Intracerebral peripheral blood stem cell (CD34+) implantation induces neuroplasticity by enhancing beta1 integrin-mediated angiogenesis in chronic stroke rats. J Neurosci. Mar. 29, 2006;26(13):3444-53.

Shyu et al., Overexpression of PrPC by adenovirus-mediated gene targeting reduces ischemic injury in a stroke rat model. J Neurosci. Sep. 28, 2005;25(39):8967-77.

Taguchi et al., Administration of CD34+ cells after stroke enhances neurogenesis via angiogenesis in a mouse model. J Clin Invest. Aug. 2004;114(3):330-8.

Taguchi et al., Circulating CD34-positive cells provide an index of cerebrovascular function. Circulation. Jun. 22, 2004;109(24):2972-5. Epub Jun. 7, 2004.

Toda et al., Immunohistochemical expression of growth factors in subacute thyroiditis and their effects on thyroid folliculogenesis and angiogenesis in collagen gel matrix culture. J Pathol. Aug. 1999;188(4):415-22. Abstract only.

Umeda et al., Simultaneous observation of stably associated presynaptic varicosities and postsynaptic spines: morphological alterations of CA3-CA1 synapses in hippocampal slice cultures. Mol Cell Neurosci. Feb. 2005;28(2):264-74. Abstract only.

Van De Ven et al., The potential of umbilical cord blood multipotent stem cells for nonhematopoietic tissue and cell regeneration. Exp Hematol. Dec. 2007;35(12):1753-65. Epub Oct. 18, 2007.

Vendrame et al., Infusion of human umbilical cord blood cells in a rat model of stroke dose-dependently rescues behavioral deficits and reduces infarct volume. Stroke. Oct. 2004;35(10):2390-5. Epub Aug. 19, 2004.

Willing et al., Intravenous versus intrastriatal cord blood administration in a rodent model of stroke. J Neurosci Res. Aug. 1, 2003;73(3):296-307.

Willing et al., Umbilical cord blood transfusions for prevention of progressive brain injury and induction of neural recovery: an immunological perspective. Regen Med. Jul. 2007;2(4):457-64. Abstract only.

Xiao et al., Transplantation of a novel cell line population of umbilical cord blood stem cells ameliorates neurological deficits associated with ischemic brain injury. Stem Cells Dev. Dec. 2005;14(6):722-33. Abstract only.

Zhang et al., Proliferation and differentiation of progenitor cells in the cortex and the subventricular zone in the adult rat after focal cerebral ischemia. Neuroscience. 2001;105(1):33-41. Abstract only.

Zhao et al., Human bone marrow stem cells exhibit neural phenotypes and ameliorate neurological deficits after grafting into the ischemic brain of rats. Exp Neurol. Mar. 2002;174(1):11-20. Abstract only.

\* cited by examiner

GFAP/Bisbenzimide

Neu-N/Bisbenzimide

MAP-2/Bisbenzimide vWF/Bisbenzimide

NG2

NG2

A2B5

CNPase

Laminin

Control (T2*)

UCB-CD34 (T2*)-2282-7 d

UCB-CD34 (T2*)-2282-14 d

MRI-T2 star and prussian blue

TREATMENT OF BRAIN DAMAGE USING UMBILICAL CORD BLOOD CELLS

RELATED APPLICATIONS

This application is a national stage filing under 35 U.S.C. § 371 of International Application No. PCT/US2009/001915 filed Mar. 26, 2009 which was published under PCT Article 21(2) in English, and which claims priority to U.S. Provisional Application Ser. No. 61/072,173, filed on Mar. 28, 2008, and entitled TREATMENT OF BRAIN DAMAGE USING UMBILICAL CORD BLOOD CELLS, the entire contents of both of which are incorporated by reference herein.

FIELD OF THE INVENTION

The invention relates to the use of umbilical cord blood cells to treat brain damage.

BACKGROUND OF THE INVENTION

Stroke refers generally to any event that blocks or reduces blood supply to all or part of the brain. It is the third leading cause of death and the leading cause of adult disability in the United States. Stroke affects about 750,000 people annually. One third of stroke patients die within the first week after the occurrence of the stroke. Of those that survive, a significant proportion are left with moderate to significant disability, including but not limited to facial, limb or total paralysis.

Various attempts have been made to treat the chronic symptoms associated with stroke. Most recently, G-CSF mobilized peripheral blood cells have been reported to treat acute and chronic stroke symptoms. There still exists a need however for treatment modalities suitable for the population at large, including those subjects for whom autologous mobilized cell therapy may not be appropriate.

SUMMARY OF THE INVENTION

The invention provides in its broadest sense a method for treating brain damage using umbilical cord blood cells. Of particular importance is the treatment of chronic stroke and neurodegenerative disease using umbilical cord blood cells. It has been surprisingly found in accordance with the invention that when umbilical cord blood cells are administered into the brain parenchyma of a chronic stroke subject, at least some of the stroke-related disability experienced by the subject is reversed.

Thus, in one aspect, the invention provides a method for treating a subject having brain tissue damage comprising administering into brain parenchyma of human subject in need thereof an isolated umbilical cord blood cell population enriched in CD34+, CD133+, or CD34+/CD133+ umbilical cord blood cells in an amount effective to treat the brain tissue damage.

In another aspect, the invention provides a method for treating chronic stroke comprising intraparenchymally administering into brain of a human subject who has had a stroke an isolated umbilical cord blood cell population enriched in CD34+, CD133+, or CD34+/CD133+ umbilical cord blood cells in an amount effective to treat the stroke, wherein the isolated population is administered more than 7 days after the stroke. In one embodiment, the population is administered more than 1 month after the stroke. In another embodiment, the population is administered more than 3 months after the stroke. In another embodiment, the population is administered more than 6 months after the stroke. In still another embodiment, the population is administered more than 1 year after the stroke.

In another aspect, the invention provides a method for treating brain tissue damage resulting from traumatic brain injury. More specifically in one embodiment, the invention provides a method for treating brain tissue damage by administering into the brain parenchyma of a subject having brain tissue damage resulting from traumatic brain injury an isolated umbilical cord blood cell population enriched in CD34+, CD133+, or CD34+/CD133+ cells. Such brain damage includes that which exists months (e.g., at least one month) or years after the occurrence of the traumatic brain injury. Accordingly, the subject may be treated (i.e., the cells may be administered to the subject) more than 1 month, more than 3 months, more than 6 months, more than 1 year, or longer, after the occurrence of the traumatic brain injury.

In still another aspect, the invention provides a method for treating a subject having a neurodegenerative disorder comprising intraparenchymally administering into brain of a human subject in need thereof an isolated population enriched in CD34+ or CD133+ umbilical cord blood cells in an amount effective to treat the neurodegenerative disorder. The neurodegenerative disorder may be but is not limited to Parkinson's disease, Alzheimer's disease, multiple sclerosis, Huntington's disease, Pick's disease, cerebellar degeneration, and amyotrophic lateral sclerosis (ALS).

In one embodiment, the isolated population is administered more than 1 month after the occurrence of the brain tissue damage or the earliest observation of such damage. In another embodiment, the isolated population is administered more than 6 months after the occurrence of the brain tissue damage or the earliest observation of such damage. In still another embodiment, the isolated population is administered more than 1 year after the occurrence of the brain tissue damage or the earliest observation of such damage.

Various embodiments apply to the aforementioned aspects and these are recited below.

In one embodiment, the population is enriched in CD34+ umbilical cord blood cells. In a related embodiment, the population comprises mononuclear cells that are at least 75% CD34+, or that are at least 90% CD34+.

In another embodiment, the population is enriched in CD133+ umbilical cord blood cells. In a related embodiment, the population comprises mononuclear cells that are at least 75% CD133+, or that are at least 90% CD133+.

In one embodiment, the population is enriched in CD34+/CD133+ umbilical cord blood cells. In a related embodiment, the population comprises mononuclear cells that are at least 75% CD34+/CD133+, or that are at least 90% CD34+/CD133+.

In one embodiment, the subject is at least 60 years of age.

In one embodiment, at least $2 \times 10^6$ cells are administered to the subject. In another embodiment, at least $5 \times 10^6$ cells are administered to the subject. And in still another embodiment, at least $8 \times 10^6$ cells are administered to the subject.

In one embodiment, the population is administered to three sites along a damaged cortical spinal tract.

In one embodiment, the population is derived from a single cord blood unit. In another embodiment, the population is derived from multiple cord blood units. In related embodiments, the population shares less than 4 out of 6 histocompatibility markers with the subject. In another embodiment, the population shares at least 4 out of 6 histocompatibility markers with the subject.

These and other aspects and embodiments of the invention will be described in greater detail herein.

BRIEF DESCRIPTION OF THE DRAWINGS

The accompanying drawings are not intended to be drawn to scale. Each identical or nearly identical component that is illustrated in various drawings is represented by a like numeral. For purposes of clarity, not every component may be labeled in every drawing.

DETAILED DESCRIPTION OF THE INVENTION

Figure 1A:
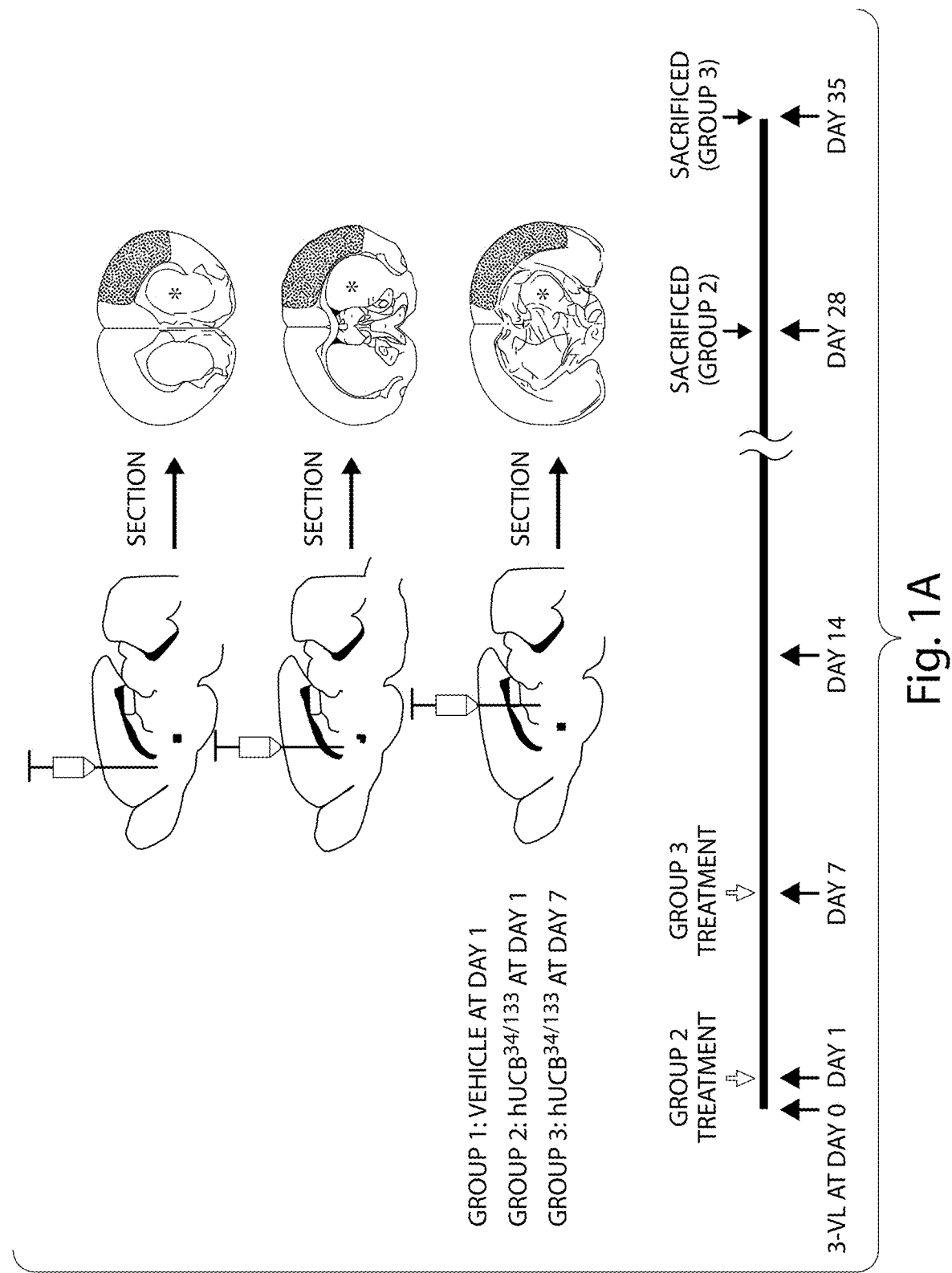
FIG. 1A is a schematic illustrating the experimental design of the model studies performed.

The invention is based, in part, on the remarkable and surprising finding that umbilical cord blood cells can reverse symptoms associated with chronic stroke. This is surprising because many of the effects of stroke heretofore either have been considered irreversible or have not been ameliorated using other treatments. The invention contemplates treatment of chronic stroke subjects even years after the occurrence of the stroke using umbilical cord blood cells.

The invention is also based in part on the finding that the umbilical cord blood cells must be administered into the parenchyma of the brain. Various aspects and embodiments of the invention provide for more particular placement of the cells into regions of the brain that are damaged as a result of the stroke. Systemic administration of the umbilical cord blood cells to these subjects has not resulted in any therapeutic benefit.

The invention is also based in part on the finding that umbilical cord blood cells expressing one or more early hematopoietic markers, such as CD34 and CD133, are particularly useful in treating chronic stroke. Thus the invention provides methods that involve administration of umbilical cord blood cells having a hematopoietic progenitor phenotype into the brain parenchyma of chronic stroke subjects. Cells having a hematopoietic progenitor phenotype are those that express either or both CD34 and CD133.

As used herein, a stroke refers to an interruption of blood supply and thus reduction in oxygen to part or all of the brain of a subject with effects that persist longer than 24 hours. Stroke may be caused by thrombosis, embolism or hemorrhage, and may be referred to as ischemic stroke (including thrombotic stroke and embolic stroke and resulting from thrombosis, embolism, systemic hypoperfusion, and the like) or hemorrhagic stroke (resulting from intracerebral hemorrhage, subarachnoid hemorrhage, subdural hemorrhage, epidural hemorrhage, and the like). As used herein, stroke excludes heat stroke and transient ischemic attacks (TIA). Heat stroke results from an elevated temperature in the body and its clinical manifestations in the brain are different from those of stroke as defined herein (i.e., interruption of blood supply associated with reduced oxygen in the brain). TIA are sometimes referred to as "mini-strokes" however they can be distinguished from stroke as defined herein due to their ability to resolve completely within 24 hours of occurrence.

Stroke is manifested by one or more symptoms in the affected subject. While these symptoms and their severity may vary from patient to patient, they generally include muscle weakness (hemiplegia), numbness, reduction in sensory and/or vibratory sensation. In many instances, these symptoms affect only one side of the body (and usually the damage exists on the other side of the brain). Other symptoms include loss of consciousness, headache, vomiting, altered smell, taste, hearing and vision (total or partial), drooping of eyelid (ptosis), weakness of ocular muscles, decreased reflexes (including gag, swallow and pupil reactivity to light reflexes), decreased sensation and muscle weakness of the face, balance problems, disequilibrium, vertigo, nystagmus, altered breathing and/or heart rate, weakness in sternocleidomastoid muscle (SCM) with inability to turn head to one side, weakness in tongue (associated with inability to protrude and/or move from side to side), aphasia (i.e., inability to speak or understand language), apraxia (i.e., altered voluntary movements), altered movement co-ordination, visual field defect, memory deficits, hemineglect, hypersexual gestures, lack of bladder or bowel control and cognitive decline (e.g., dementia, disorganized thinking, confusion, limited attention span, inability to concentrate), and altered walking pattern. Some hallmark symptoms of stroke include acute facial paresis, arm drift and abnormal speech. Patient symptoms are usually graded using a pre-established scoring system such as but not limited to the National Institutes of Health Stroke Scale (NIHSS).

Stroke is diagnosed through neurological examination, blood tests, and/or medical imaging techniques such as CT scans (e.g., without contrast agents), MRI scans, Doppler ultrasound, and arteriography.

As used herein, acute stroke refers to the one or more symptoms and/or one or more risks experienced by an affected subject immediately (i.e., within the first seven day period) after the occurrence of the stroke. The major risk is death since approximately one third of subjects die within this seven day window. Symptoms experienced during this time period include many of those listed above including but not limited to abnormal speech, arm drift, loss of consciousness, headache, vomiting, drooping of eyelid (ptosis), balance problems and disequilibrium, acute facial paresis, and the like. For some patients, timely intervention can reduce the severity and number of symptoms.

A significant proportion of patients however continue to experience one or more of these symptoms in the long term and it is these patients for whom the invention is intended. These patients are considered to suffer from chronic stroke (or are referred to as chronic stroke patients) because their stroke symptoms exist beyond the acute phase (i.e., they persist for more than 7 days and/or they are manifest beyond 7 days following the occurrence of the stroke). Thus as used herein, chronic stroke refers to the one or more symptoms and/or one or more risks that are associated with the initial stroke event and that exist in patients who had a stroke more than 7 days prior. Generally the severity and collection of these symptoms lead to disability in the patient. For example, chronic stroke patients may be unable to speak or understand language, they may be unable to walk or may walk with difficulty (as evidenced by gait tracings), they may have altered or impaired facial muscle control, they may have altered or impaired overall muscle control resulting in lack of co-ordinated movement or control of extremities, they may have impaired vision, they may be partially or completely paralyzed, they may be in a coma, and the like.

It has been shown according to the invention that such subjects greatly benefit from the administration of umbilical cord blood cells into the brain parenchyma. The inventors have demonstrated that chronic stroke subjects treated in this manner regain control of their muscular function as evidenced by a more regular (or normal) walking gait or pattern, and/or greater extremity control.

The methods of the invention can be used on any patient who has had a stroke more than 7 days prior to treatment and who continues to experience one or more symptoms associated with the stroke. The invention contemplates treating such patients at any time beyond the acute phase. Thus patients may be treated within the second week after the stroke occurrence (i.e., 8, 9, 10, 11, 12, 13 or 14 days after the occurrence of the stroke). In some important embodiments, patients may be treated more than two weeks (i.e., 15, 16, 17, 18, 19, 20 or 21 days after the occurrence of the stroke), more than three weeks, or more than four weeks after the occurrence of the stroke. Still other patients may be treated 1, 2, 3, 4, 5 or 6 months after the occurrence of the stroke, and other patients may be treated beyond the 6 month period including 7, 8, 9, 10, 11, or 12 months after the occurrence of the stroke or 1, 2, 3, 4, 5 or more years after the occurrence of the stroke. As used herein, treatment at for example 1 year after the occurrence of the stroke means that at a minimum 1 year has passed since the patient had the stroke. It does not mean that treatment occurs at the one year anniversary of the stroke. The injury in many of these patients may have been deemed irreversible or untreatable prior to the invention.

The patients to be treated according to the invention can be identified based on their stroke history (i.e., the time between the occurrence of the stroke and the time of treatment) and optionally on their stroke score. A stroke score is a numerical representation of the severity of the symptoms experienced by the patient. NIHSS, ESS, EMS and Barthel index are all scoring systems for determining the severity of stroke symptoms in a patient. In the case of the NIHSS, lower scores indicate fewer symptoms and less disability. While the methods described herein can be used to treat any stroke patient, preferably they are used to treat patients with more severe symptoms. Thus, in one embodiment, patients having a NIHSS score of 9-20 are treated according to the invention, including patients having NIHSS scores of 9, 10, 11, 12, 13, 14, 15, 16, 17, 18, 19, and 20. An example of a patient having an NIHSS score of 9 is a patient who responds only with reflex motor or autonomic effects, is mute (i.e., has no usable speech or auditory comprehension), and has complete paralysis of one or both sides of the face (i.e., absence of facial movement in the upper and lower face). A medical practitioner would be knowledgeable of such scores and thus could readily identify subjects that can be treated according to the invention using the timing and stroke score guidance provided herein.

The invention contemplates treatment of subjects having neurodegenerative disorders also. A neurodegenerative disorder is a disorder characterized by progressive deterioration and/or death of neurons. Examples include but are not limited to Parkinson's disease, Alzheimer's disease, multiple sclerosis, Huntington's disease, Pick's disease, Creutzfeldt-Jakob disease, progressive supranuclear palsy (PSP), parkinsonism, Shy-Drager syndrome, cerebellar cortical atrophy, Friedrich ataxia, dentatorubral degeneration, Machado-Joseph disease, spinal muscular atrophy, pallidopontonigral degeneration (PPND), pallidonigroluysian degeneration (PNLD), amyotrophic lateral sclerosis (ALS), Guam-ALS syndrome, corticobasal degeneration (CBD), epilepsy, ischemic brain injury, senile dementia, Korsakov's syndrome, pontocerebellar atrophy, olivopontocerebellar atrophy or degeneration, glutaric acidaemia, diffuse Lewy body dementia, frontotemporal dementia with parkinsonism linked to chromosome 17 (FTDP-17), multi-infarct dementia, brain inflammation, multiple system atrophy (MSA), and pallidal degeneration.

The invention also contemplates the treatment of subjects having chronic brain damage resulting from traumatic brain injury (TBI).

The methods of the invention can be performed on any patient regardless of age or sex, although it is expected that elderly subjects may particularly benefit. As used herein, an elderly patient is one who is 60 years of age or older. It will be understood in the context of this description that the preferred subjects are human subjects.

As used herein, treating a subject having chronic stroke means ameliorating, reducing or completely eliminating one or more chronic stroke symptoms. As an example, a subject having a stroke is treated according to the invention to reduce the extent of brain injury resulting from the stroke. Brain injury can be measured by determining an infarct size using standard medical imaging techniques. A reduction in the extent of brain injury can therefore be measured as a decrease in the infarct size as viewed using these imaging techniques. In some instances, the infarct area (or volume) may decrease by at least 5%, 10%, 20%, 30%, 40%, 50%, 60%, 70%, 80%, 90%, 95% or it may disappear completely. In preferred embodiments, the treatment reduces the infarct area by at least 10%. Likewise, tests measuring neurological function can be used to determine the extent of brain injury. Scoring systems such as the NIHSS can also be used to assess treatment in a subject. As an example, a 1, 2, 3, 4, 5, 10, 15, or 20 point reduction in an NIHSS score would all be indicative of treatment. In preferred embodiments, the treatment results in at least a 4 point reduction. In other embodiments, treatment results in an NIHSS score of 0-8.

The methods of the invention involve administration of umbilical cord blood cells to subjects. Umbilical cord blood cells are cells harvested from the veins and arteries of an umbilical cord. Methods for extracting such cells from umbilical cords are known in the art and have been published. (See for example US Published Application No. 20060275271.) These cells may be harvested and frozen prior to use or they may be used without freezing. Methods for freezing such cells are also known in the art and have been published. (See for example US Published Application No. 20060275271.)

As used herein, an isolated cell population is a cell population that has been physically separated from the environment and/or the context in which it naturally occurs or exists. Thus, once the umbilical cord blood cells are removed from the umbilical cord, they are considered isolated.

In important embodiments of the invention, the umbilical cord blood cells are fractionated in order to generate enriched cell populations. As used herein, an enriched cell population is a cell population that has been manipulated in order to increase the frequency of a particular cell type in the population relative to the frequency of that cell type prior to manipulation. It is to be understood that the cell type being enriched is one that existed in the population prior to manipulation, and that enrichment results from the removal of other cell types from the population rather than addition of the cell type of interest. Of particular interest according to the invention are cell populations enriched in CD34+, CD133+, or CD34+/CD133+ cells. CD34 and CD133 are cell surface protein (or markers) that have been identified previously as present on hematopoietic progenitor cells (including on hematopoietic stem cells). As used herein, a CD34+ cell is a cell that expresses CD34 on its cell surface. Similarly, a CD133+ cells is a cell that expresses CD133 on its cell surface. A CD34+/CD133+ cell is a cell that expresses both CD34 and CD133 on its surface. CD34+ and CD133+ cells each represent approximately 0.1% of all mononuclear umbilical cord blood cells. Moreover, there is considerable overlap between the CD34+ and CD133+ cell populations, such that many CD34+ cells also express CD133, and vice versa. As used herein, populations that are enriched in CD34+ cells, CD133+ cells, or CD34+/CD133+ cells are populations in which CD34+ cells, CD133+ cells, or CD34+/CD133+ cells respectively represent at least 60% of the mononuclear cells in the population. These populations may have even higher frequencies of the particular cell types. For example, the mononuclear fraction of these populations may be at least 65%, 70%, 75%, 80%, 85%, 90%, 91%, 92%, 93%, 94%, 95%, 96%, 97%, 98% or 99% CD34+, CD133+ or CD34+/CD133+. As an example, a cell population that is at least 75% CD34+ is a population in which at least 75% of its mononuclear cells express CD34. In preferred embodiments, the administered population is at least 90% CD34+, at least 90% CD133+, or at least 90% CD34+/CD133+.

Methods for preparing cell populations enriched in particular cell types are known in the art. In the case of cell populations that are defined by a cell surface marker (such as CD34+, CD133+, and CD34+/CD133+ cells), these methods generally use antibodies that are specific for the expressed marker(s). These antibodies can be attached to a number of solid supports including plates (e.g., in panning methods), column matrices (e.g., in column enrichment methods), magnetic beads (e.g., in magnetic separation methods), and the like. These supports are then contacted with the cell population of interest and cells expressing the marker of interest are allowed to bind to the antibody, while the remaining unbound cells are removed. The bound cells are then removed by any number of techniques (e.g., enzymatic, mechanical, competitive binding, temperature, etc.). Enriched populations can also be produced by contacting cells with the antibody of interest and then sorting cells based on the presence or absence of the antibody using fluorescence activated cell sorting. The presence of the antibody is generally observed by labeling the antibody with a fluorescent probe (e.g., FITC) or by contacting the cells with a second antibody that recognizes the first antibody and is itself labeled with a fluorescent probe. These methods, as well as others, are known in the art and those of ordinary skill will be able to readily enrich the desired populations.

Anti-CD34 antibodies include but are not limited to QBend10, 563, HPCA-2, 581, AC136, and Birma K3. Anti-CD133 antibodies include but are not limited to ANC9C5. These antibodies are commercially available from sources such as R&D Systems, Santa Cruz Biotechnology.

The isolated enriched populations are administered to patients in amounts (or numbers) effective to treat the patient, as described herein. The numbers of cells necessary for treatment will depend on a number of factors including the severity of the symptoms experienced by the subject (as may be deduced from for example an NIHSS score), the size (or area) of the infarct as determined using a medical imaging technique such as MRI, the degree of enrichment of the desired cell type in the administered population, the age and/or weight of the patient, and the like. Generally, it is expected that cell numbers in the range of 1 to $10\times10^6$, and more preferably 2 to $8\times10^6$ can be administered to the patients. Thus depending on the particular patient and the population being administered, the number of cells administered can be about $2\times10^6$, about $3\times10^6$, about $4\times10^6$, about $5\times10^6$, about $6\times10^6$, about $7\times10^6$, or about $8\times10^6$. These amounts may refer to the total number of CD34+, CD133+ or CD34+/CD133+ cells, or the total mononuclear cells administered to the subject, depending on the embodiment and the degree of enrichment in the cells.

The cells to be administered may be provided in a single cord blood unit although in some instances multiple cord blood units must be combined to achieve the cell numbers being administered. As used herein, a cord blood unit is the amount of cord blood harvested from a single cord. Typically, each cord blood unit contains approximately $120-150\times 10^7$ mononuclear cells, of which only about 0.1% are CD34+ and/or CD133+.

Regardless of whether one or multiple units are administered to a subject, it may be advisable in some instances to administer cells that are histocompatible with the subject being treated. As used herein, histocompatibility means that at least 4 out of 6 major histocompatibility markers are shared by the cells being transplanted and the subject being treated. Clearly, the invention also contemplates situations in which the cells and subject share 5 or even 6 of the same histocompatibility markers. It has also been found according to the invention that in some instances cells that share fewer than 4, fewer than 3, fewer than 2, or no histocompatibility markers with the subject can still be therapeutically beneficial to that subject. Histocompatibility markers include the class I markers HLA-A, HLA-B and HLA-C, the class II markers HLA-DP, HLA-DQ and HLA-DR, and the nonclassical class I markers HLA-E, HLA-F, HLA-G, HLA-H, HLA-J and HLA-X, MIC. In some embodiments, the 6 histocompatibility markers may be HLA-A, HLA-B, HLA-C, HLA-DR, HLA-DQ, and HLA-DP. Other combinations are also contemplated.

Since the population is administered into the brain parenchyma, it is also important to administer the population in as small a volume as reasonably possible. The administered volume may vary depending on the age and/or weight of the patient, and the number of cells being administered, among other factors. Generally, the amount administered is less than 1 mL, preferably less than 0.75 mL, and more preferably about or less than 0.5 mL. In some instances, 0.4, 0.3, or 0.2 mL are administered.

The cell population is administered into the brain parenchyma (i.e., the tissue of the brain). In this regard, such administration is referred to as intraparenchymal administration. Preferably, the cells are deposited into the brain parenchyma, preferably in and/or around the area of damage, and may include regions that are peripheral to the area of damage as well as the boundary of the area of damage.

Even more preferably, aliquots of the total administered population are deposited in two, three, or more positions in the brain parenchyma. As an example, the cells may be deposited along an involved or affected corticospinal tract, with one deposit made beyond the area of damage, one deposit made in the center of area of damage, and one deposit made between the area of damage and the skull. The area of deposit can be determined using stereotactic devices. The co-ordinates for injection and deposit of cells will vary between patients, but will be readily determinable by those of ordinary skill in the art.

The cells may be administered to the brain parenchyma using for example a 26 gauge Hamilton syringe, or an equivalent syringe or device. For purposes of illustration, in one embodiment, the syringe is loaded with the cells and the needle is inserted into the brain parenchyma along the damaged corticospinal tract until its tip reaches a position that is beyond (or at the boundary of) the area of damage. Approximately one third of the cells (or similarly of the volume in the syringe barrel) are deposited at this position. The needle is then retracted until its tip reaches a position that is in the area of damage (preferably but not necessarily at or near the center of the damage) at which point another third of the cells (or volume in the syringe barrel) is deposited. The needle is then again retracted until its tip reaches a position that is behind (or at the boundary of) the area of damage. The remaining third of cells (or volume in the syringe barrel) is deposited at this position. The needle is then retained in place for about 5 minutes after each deposition. Once the needle is completely retracted, the site of entry is plugged in order to prevent leakage (and loss) of the injected volume. This can be accomplished by using bone wax, as an example. It is to be understood however that the invention contemplates a single transplant of cells into the damaged brain, rather than a multi-day administration regimen.

The cells are suspended in and administered with a pharmaceutically acceptable carrier, and in this form are considered pharmaceutical compositions or preparations. As used herein, a pharmaceutically-acceptable carrier means one or more compatible liquid fillers, diluents, and the like, which are suitable for administration into a human. As used herein, carrier means an organic or inorganic ingredient, natural or synthetic, with which the active ingredient is combined to facilitate efficacy and/or administration. The pharmaceutical preparations may contain suitable buffering agents, including but not limited to acetic acid in a salt; citric acid in a salt; boric acid in a salt; and phosphoric acid in a salt. The pharmaceutical compositions also may contain, optionally, suitable preservatives, such as benzalkonium chloride, chlorobutanol, parabens and thimerosal. The components of the pharmaceutical compositions are commingled with cell population, and with each other, in a manner such that there is no interaction which would substantially impair the desired pharmaceutical efficacy. The pharmaceutical compositions or preparations may also comprise other substances including non-cellular agents that either are themselves therapeutically effective or which enhance the therapeutic efficacy of the administered cells. These components may be provided together in a vial, in separate vials in a kit, or in separate kits.

Compositions suitable for administration may comprise a sterile aqueous suspension of cells, which is preferably isotonic with the blood of the recipient. This aqueous preparation may be formulated according to known methods using suitable dispersing or wetting agents and suspending agents. The sterile injectable preparation also may be a sterile injectable solution or suspension in a non-toxic parenterally-acceptable diluent or solvent, for example, as a solution in 1,3-butane diol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or di-glycerides. In addition, fatty acids such as oleic acid may be used in the preparation of injectables. Carrier formulation suitable for oral, subcutaneous, intravenous, intramuscular, etc. administrations can be found in Remington's Pharmaceutical Sciences, Mack Publishing Co., Easton, Pa.

EXAMPLES

Materials and Methods

Purification and selection of $CD34^+/133^+$ hUCBs ($hUCB^{34/133}$).

Mononuclear cells (MNCs) were prepared from whole human umbilical cord blood ($hUCB^W$) (Stemcyte, USA). The MNC layer was collected and washed twice with 1 mM EDTA in PBS. Both $CD34^+$ and $CD133^+$ MNCs were separated from $2 \times 10^8$ MNCs by a magnetic bead separation method (MACS; Miltenyi Biotec, Gladbach, Germany) according to the manufacturer's instructions. In brief, MNCs were suspended in 300 µL PBS and 5 mM EDTA. These cells were labeled with hapten-conjugated monoclonal antibodies against CD34 and CD133 (Miltenyi Biotec, Gladbach, Germany), followed by an anti-hapten antibody coupled with microbeads at ratios of 100 µL beads per $10^8$ cells for 15 minutes at 4° C. The bead-positive cells (i.e., $CD34^+$ and $CD133^+$ MNCs) were enriched on positive-selection-columns set in a magnetic field. FACS analysis using anti-CD34 and anti-CD133 antibodies (Miltenyi Biotec, Gladbach, Germany) labeled with phycoerythrin (PE) (Becton Dickinson, USA) of MACS-sorted cells showed that 90%±3% of the selected cells were positive for both CD34 and CD133 as shown in FIG. 1B. Then, cells labeled with 1 µg/mL bisbenzimide (Hoechst 33342; Sigma, USA), resuspended in 3004 Iscove's Modified Dulbecco's Medium (Gibco/Invitrogen, UK) plus 2% FBS (Hyclone, Road Logan, Utah) were mixed with 3 ml MethoCult GF H4434 containing recombinant cytokines and erythropoietin (StemCell Technologies, USA) at 37° C. in a humidified atmosphere of 5% $CO_2$/95% air and antibiotics for one hour, and prepared for transplantation.

Rat Experimental Stroke Model.

Thirty adult male Sprague-Dawley rats weighing about 250-300 g were subjected to three-vessel ligation. All surgical procedures were performed using sterile/aseptic techniques in accordance with University Institutional guidelines. The rats were anesthetized with chloral hydrate (0.4 g/kg) intraperitoneally. Ligation of the right middle cerebral artery (MCA) and bilateral common carotids (CCAs) was performed on day 0 by a method modified from that described by Chen et al. (Stroke, 1986, 17 (4):738-743). CCAs were clamped with non-traumatic arterial clips. Under a surgical microscope, a 2×2 craniotomy was drilled where the zygoma fuses to the squamosal bone. The right MCA was ligated with an 10-0 nylon suture. Cortical blood flow was measured continuously with a laser Doppler flowmeter (PF-5010, system, Perimed system, Perimed AB, Stockholm, Sweden) in anesthetized animals. A burr hole (1 mm diameter) was made in the right frontoparietal region to allow placement of photodetectors. A probe (0.45 mm in diameter) was stereotaxically placed in the cortex (1.3 mm posterior, 2.8 mm lateral to the bregma, and 1.0 mm below the dura). After 90 minutes of ligation, the suture on the MCA and arterial clips on CCAs were removed to allow reperfusion. The core body temperature was monitored with a thermistor probe and maintained at 37° C. with a heating pad during anesthesia. After each rat recovered, the body temperature was maintained at 37° C. with a heat lamp. As expected, all of the rats developed significant body asymmetry and turned contralateral to the side of the ischemic brain on day 1 following cerebral ischemia and prior to any cell administration.

Experimental animals treated with intracerebral $hUCB^{34/133}$ cells or vehicle.

Figure 1B:
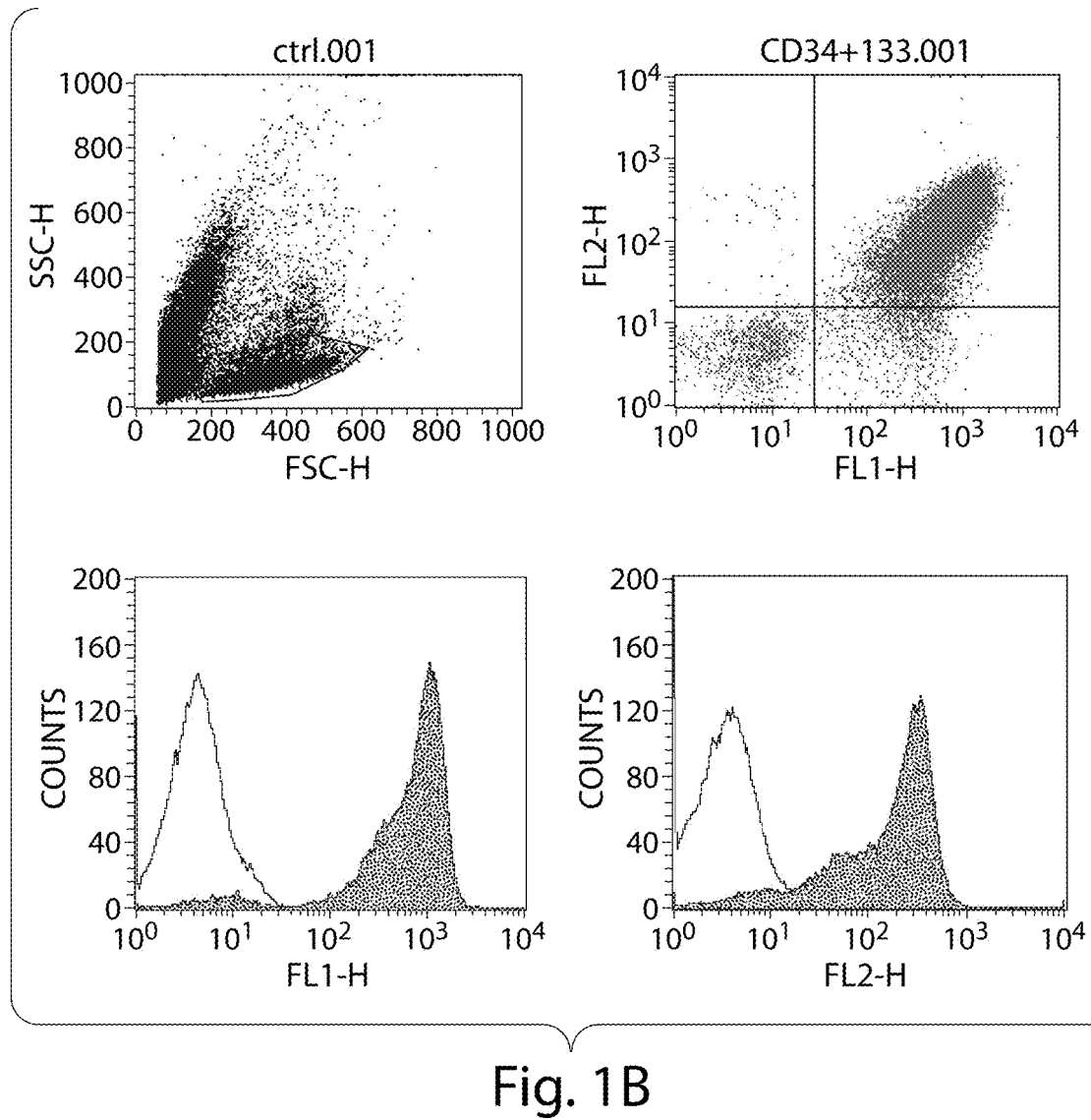
FIG. 1B are a series of graphs showing the phenotype of cell populations enriched in CD34 and CD133.

Rats were then divided into three groups as shown in FIG. 1A. Group 1 was administered vehicle alone on day 1 post experimental stroke. Group 2 was administered $hUCB^{34/133}$ cells on day 1 post experimental stroke. This group represents an experimental model of acute stroke since the cells are administered 1 day post experimental stroke. Group 3 was administered $hUCB^{34/133}$ cells on day 7. This group represents an experimental model of chronic stroke. Cells or vehicle alone were injected stereotaxically into the damaged pyramidal tracts of the caudateputamen. Approximately $2 \times 10^5$ $hUCB^{34/133}$ cells labeled with bisbenzimide cells suspended in a 3-5 µL PBS were injected into 3 cortical areas, 3-5 mm below the dura, using a 26-gauge Hamilton syringe. The approximate coordinates of the cortical sites are (1) 1.0 to 2.0 mm anterior to the bregma and 3.5 to 4.0 mm lateral to the midline, (2) 0.5 to 1.5 mm posterior to the bregma and 4.0 to 4.5 mm lateral to the midline, and (3) 3.0 to 4.0 mm posterior to the bregma and 4.5 to 5.0 mm lateral to the midline. The needle was retained in place for 5 minutes after each injection and a piece of bone wax was applied to the skull defects to prevent leakage of the injected solution. Experimental rats in the vehicle group were treated with saline stereotaxically. Daily cyclosporin A (10 mg/kg, ip, Novartis) injections were administered to each experimental rat, while the vehicle controls received an equivalent volume of saline as previously described (Zhao et al., 2004).

Results

Neurological Functioning and Other Behavioral Assessment.

To evaluate neurological function in the three experimental groups of rats, behavioral assessments were carried out 3 days before cerebral ischemia (i.e., on day-3), and 1, 7, 14, 21, 28 and 35 days after the ischemic injury. The assessments measured (a) body asymmetry, (b) locomotor activity, and (c) grip strength. The baseline-test scores were recorded in order to normalize those taken after cerebral ischemia.

The elevated body swing test (EBST) was used to quantitatively assess body asymmetry after MCA ligation in the manner described by Borlongan et al. (Neuroreport, 1998, 9 (12):2837-2842). Initially, each rat was examined for lateral movement while its body was suspended by the tail. The frequency of initial head swing contra-lateral to the ischemic side was counted in twenty continuous tests and normalized in the manner described by Chang et al. (Stroke. 2003; 34 (2):558-564).

In locomotor activity tests, each rat was subjected to Animal Activity monitoring (Accuscan Instruments, Inc., Columbus, Ohio) for about 2 hours for behavioral recording. The Animal Activity monitor contained 16 horizontal and 8 vertical infrared sensors spaced 87 cm apart. The vertical sensors were situated 10 cm from the floor of the chamber. Locomotor activity was counted as the number of beams broken by rat movement in the chamber. Three vertical parameters defined in the manufacturer's menu option were calculated over 2 hours at night: (i) vertical activity, (ii) vertical time, and (iii) number of vertical movements.

Figure 2:
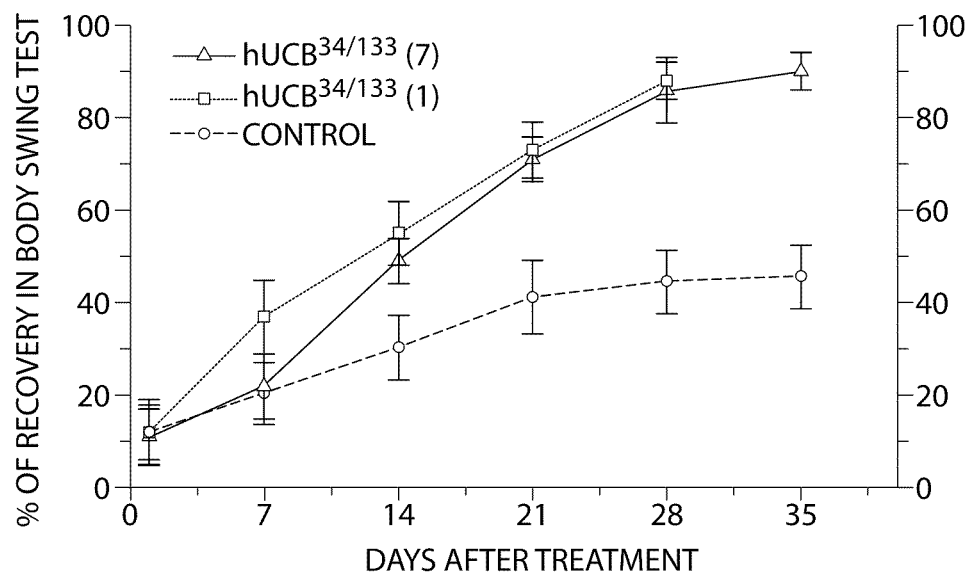
FIG. 2 is a graph showing recovery of body swing as a function of time in the two experimental and one control group.
Figure 3A:
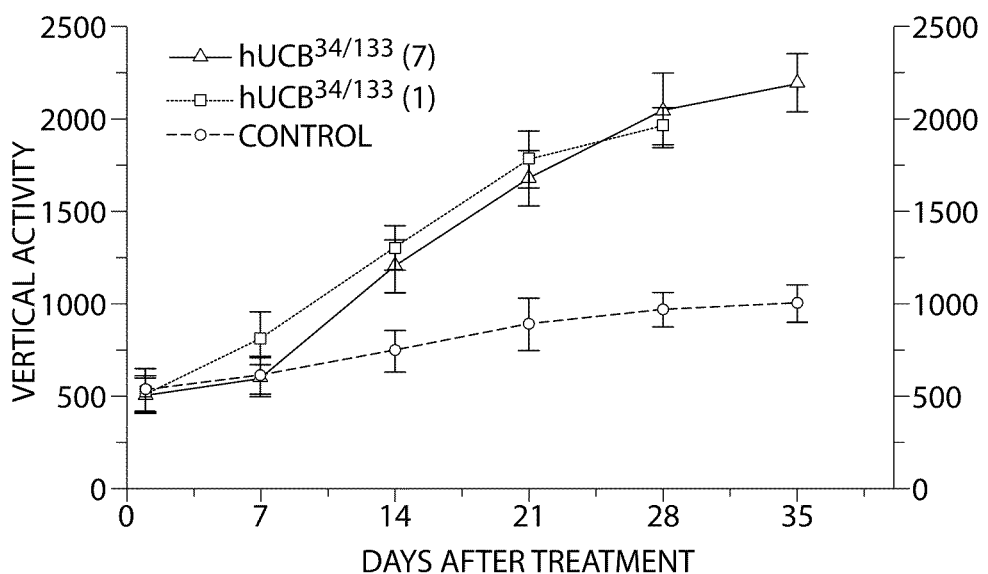
FIG. 3A is a graph showing vertical activity as a function of time in the two experimental and one control group.
Figure 3B:
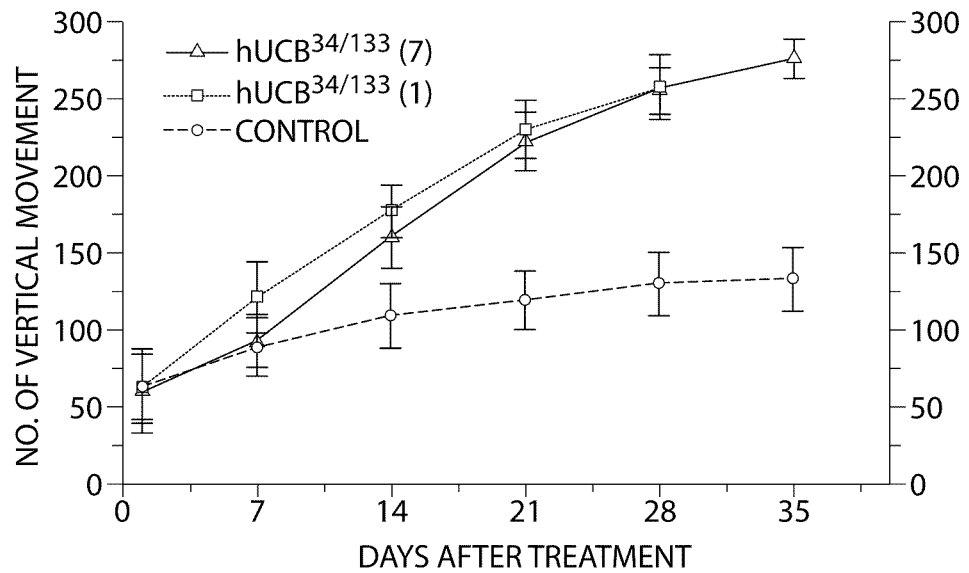
FIG. 3B is a graph showing number of vertical movements as a function of time in the two experimental and one control group.
Figure 3C:
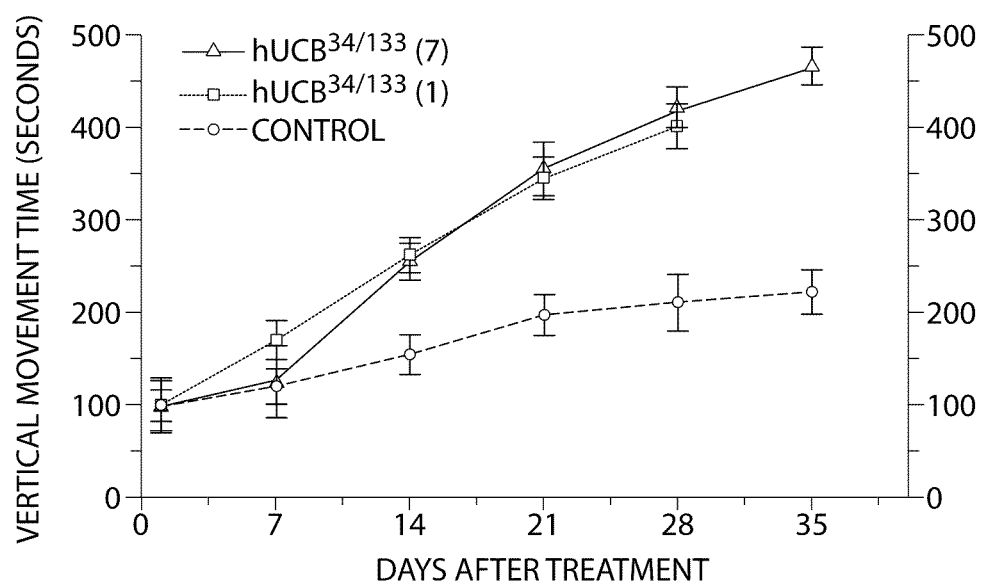
FIG. 3C is a graph showing vertical movement time as a function of time in the two experimental and one control group.

The behavioral measurement scores were all normalized against the baseline scores. It was found that, 14 to 28 or 35 days after treatment, rats treated with hUCB exhibited significantly reduced body asymmetry in comparison with control rats as shown in FIG. 2. Rats in the hUCB groups also showed significant increases in vertical activity (FIG. 3A), the number of vertical movements (FIG. 3B), and vertical movement time (FIG. 3C) in comparison with control rats.

Figure 4:
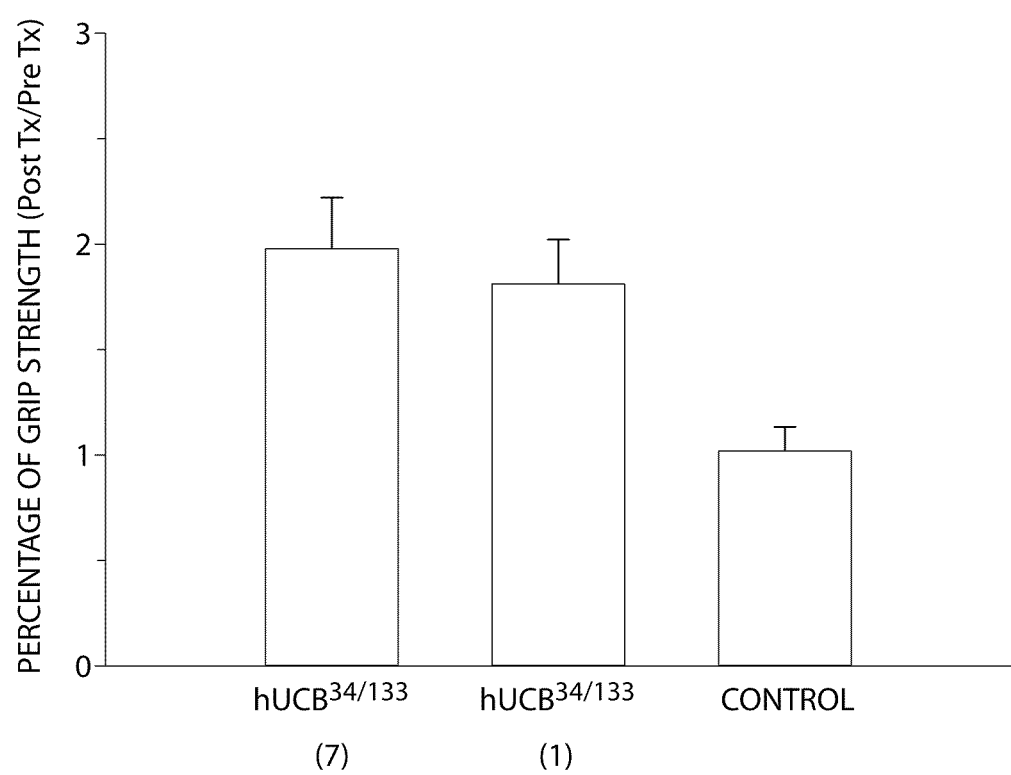
FIG. 4 is a graph showing percentage of grip strength in the two experimental and one control group.

Grip strength was analyzed using a Grip Strength Meter (TSE-Systems, Germany) by a method modified from that described by Stephen (Neurosci. Lett. 1998, 264:1-4). Briefly, grip strength ratio was measured on each forelimb and calculated as the ratio between the mean strength out of 20 pulls of the side contralateral to the ischemia and that of ipsilateral side. In addition, the ratio of grip strength before the treatment ("Pre Tx") and after the treatment (day 28; "Post Tx") and baseline were also calculated and changes are presented as a percentage of baseline value. It was found that ratios were about 0.95, 1.8 and 1.95 for Groups I (control), 2 (administration at 1 day), and 3 (administration at day 7) as shown in FIG. 4. The grip strength results reveal that rats administered hUCB showed a higher ratio of grip strength than the untreated control rats.

Brain metabolism and anatomy.

Figure 5:
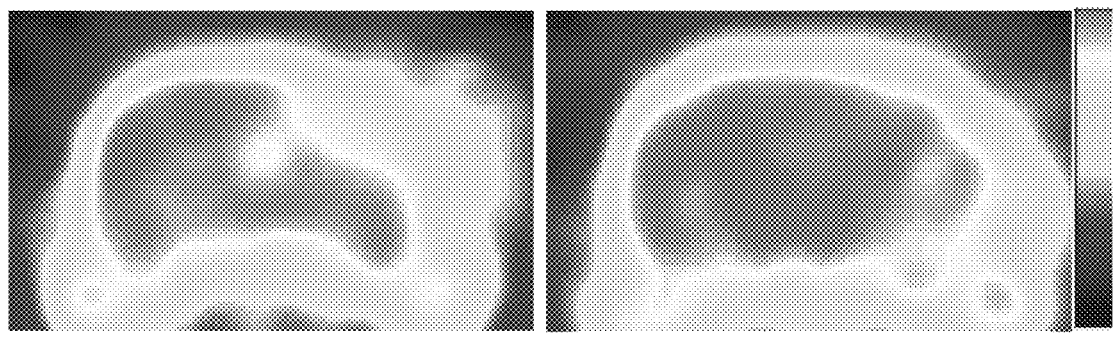
FIG. 5 is PET images of the brain of rats in control and experimental animals.
Figure 6:
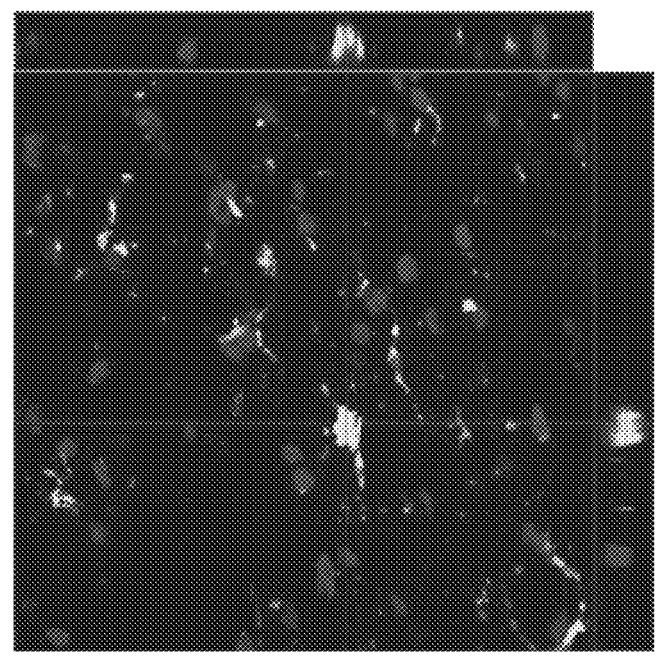
FIG. 6 is photograph showing brain tissue sections stained for GFAP or Neu-N (green) and bisbenzimide (blue).
Figure 6:
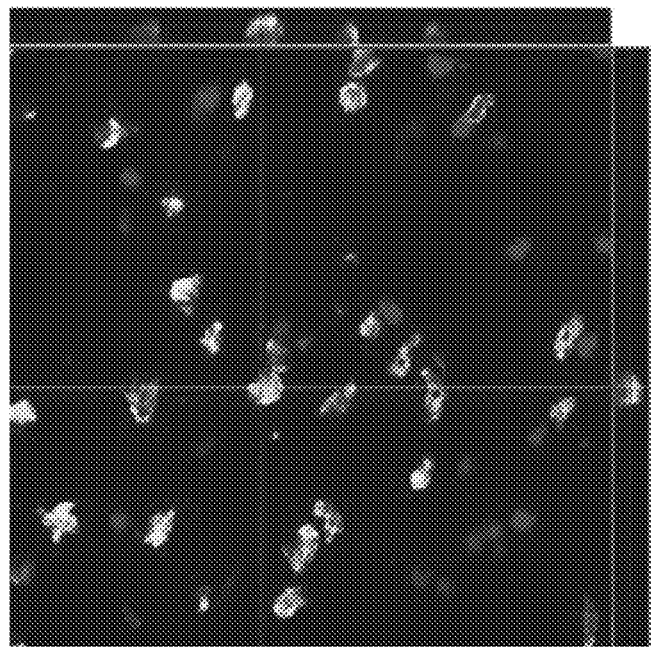
Figure 12:
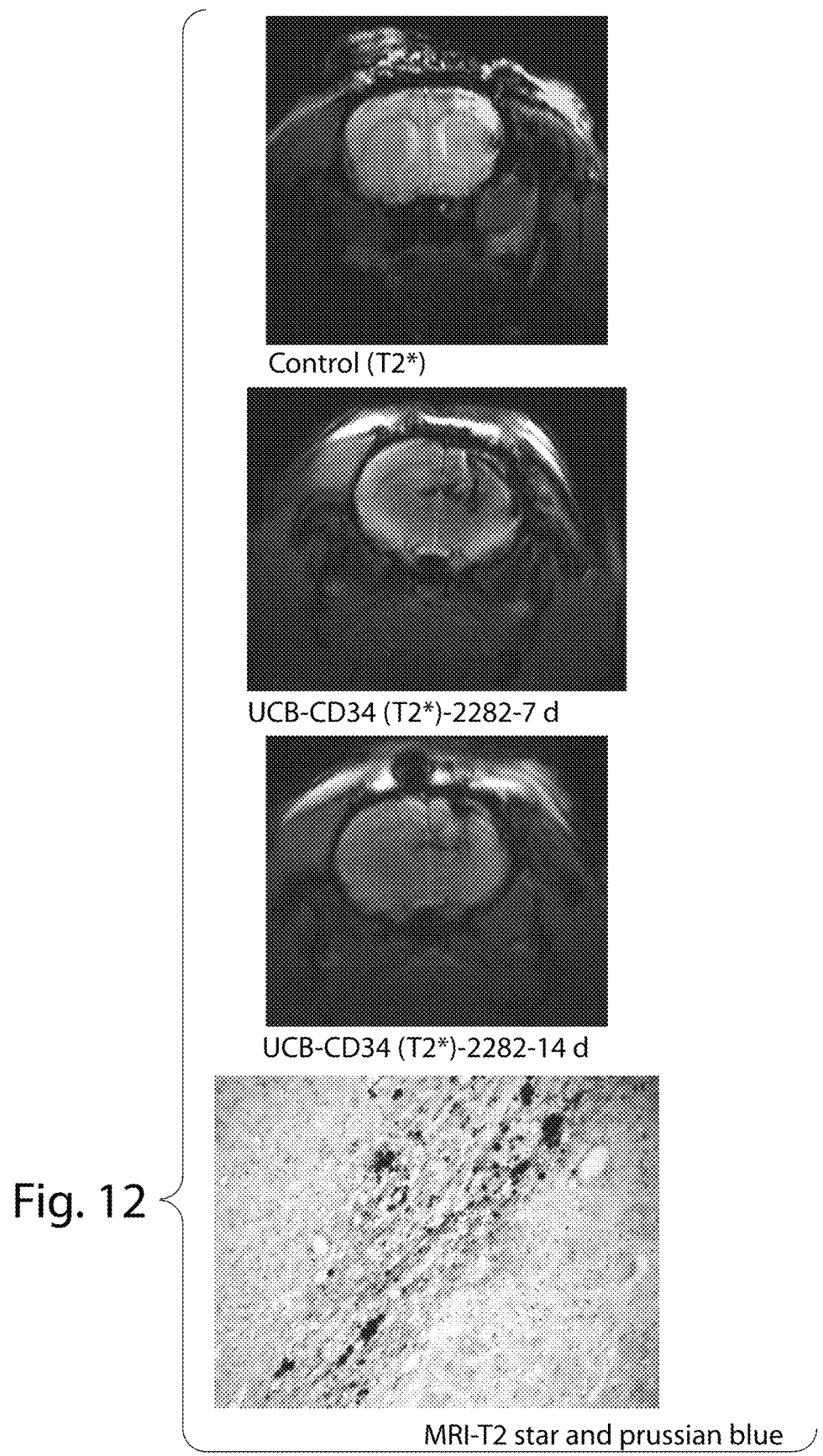
FIG. 12 shows MRI-T2 scans and a Prussian blue stain of a brain tissue section from chronic stroke animals. Cortical infarction is noted in the chronic stroke animal. The injected stem cells were noted in the right basal ganglia region 7 days after the injection. These cells migrated along the nerve fibers to the infarct region, the size of which diminished 14 days after the transplantation.

FIG. 5 shows brain metabolism as monitored by FDG PET scan, in control and treated animals. FIG. 12 shows the MRI brain scans of control and treated mice.

Immunohistochemistry.

Immunofluorescent staining was conducted to determine whether the administered hUCB cells could differentiate into neurons, glial cells, or endothelial cells in ischemic brains. Confocal microscopy was carried out to identify whether cell type-specific markers co-localized with exogenous transplanted (bisbenzimide-labeled). The rats were anesthetized with chloral hydrate (0.4 g/kg, ip) and their brains fixed by transcardial perfusion with saline, followed by perfusion and immersion in 4% paraformaldehyde and embedded in 30% sucrose. A series of adjacent 20-pm-thick sections were cut from each brain in the coronal plane.

Each coronal section was incubated with cell type-specific antibodies: glial fibrillary acidic protein ("GFAP," for astrocyte, 1:400, Sigma), Von-Willebrand factor ("vWF", for endothelial cell, 1:400, Sigma), neuronal nuclear antigen ("Neu-N," for neuronal nuclei, 1:200, Chemicon), microtubule-associated protein 2 ("MAP-2," for neuronal dendrites, 1:200, BM), CXCR4 (CD 184, 1:100, Toney Pines Biolab), or Doublecortin (Dcx, 1:100, Santa Cruz Biotechnology) with Cy3 (Jackson Immunoresearch PA USA, 1:500) staining.

The results showed that some bis-benzimide labeled cells (blue, cell nuclei fluoresce spontaneously) colocalized with antibodies against MAP-2, Neu-N and GFAP (green, neural cell-type specific markers) in the penumbra of hUCB-treated ischemic rat brains (FIGS. 6-11).

Figure 7:
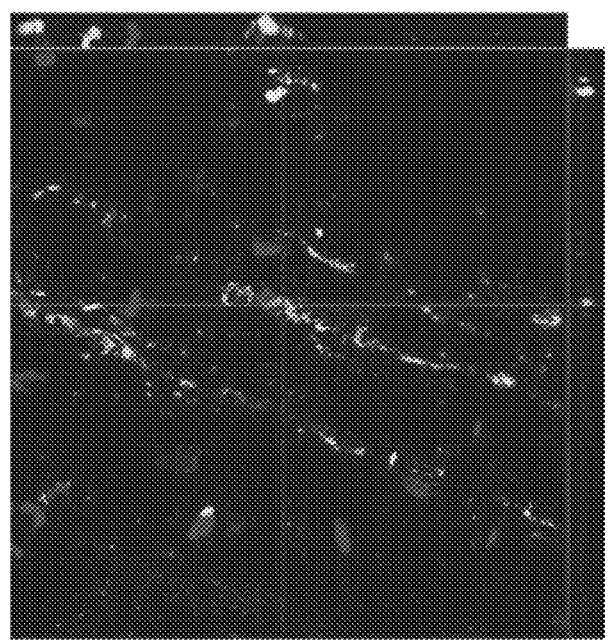
FIG. 7 is an image showing brain tissue sections stained for MAP-2 or vWF (green) and bisbenzimide (blue).
Figure 7:
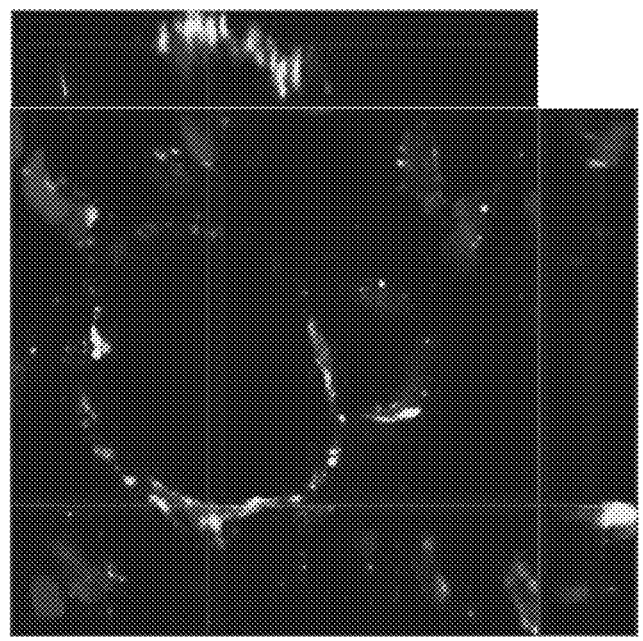
Figure 8A:
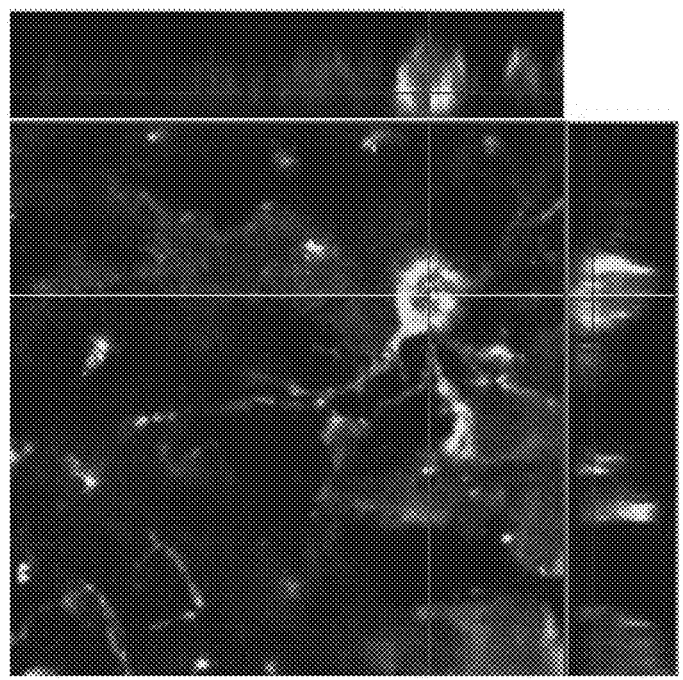
FIGS. 8A and 8B are images showing brain tissue sections stained for NG2 (green) and bisbenzimide (blue).
Figure 8B:
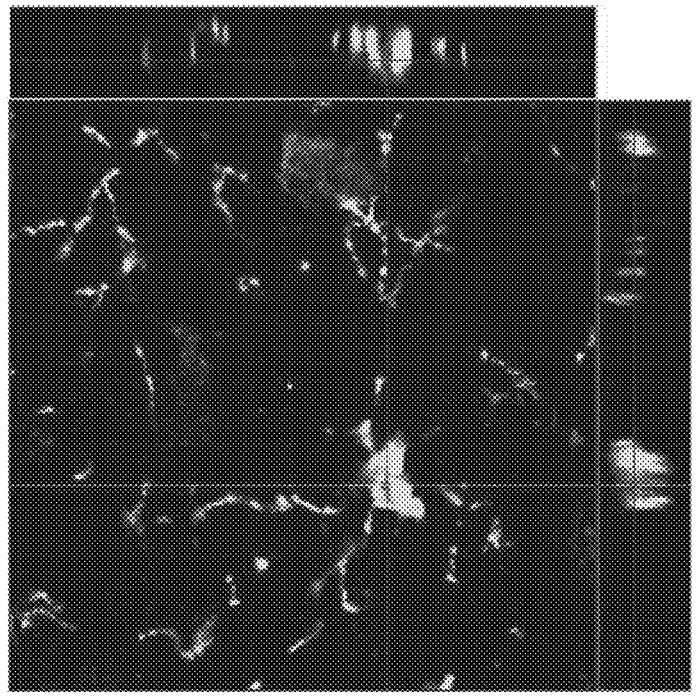
Figure 9:
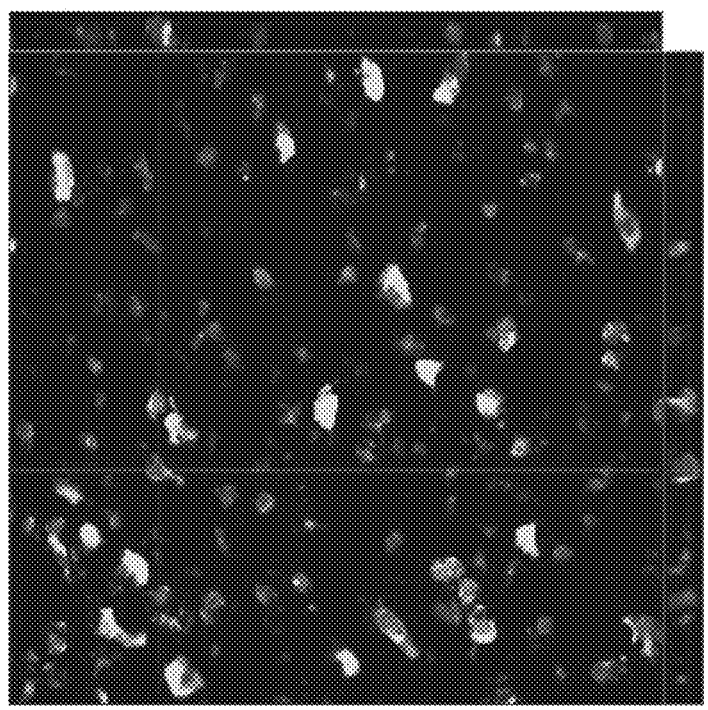
FIG. 9 is an image showing brain tissue sections stained for A2B5 (green) and bisbenzimide (blue).
Figure 10:
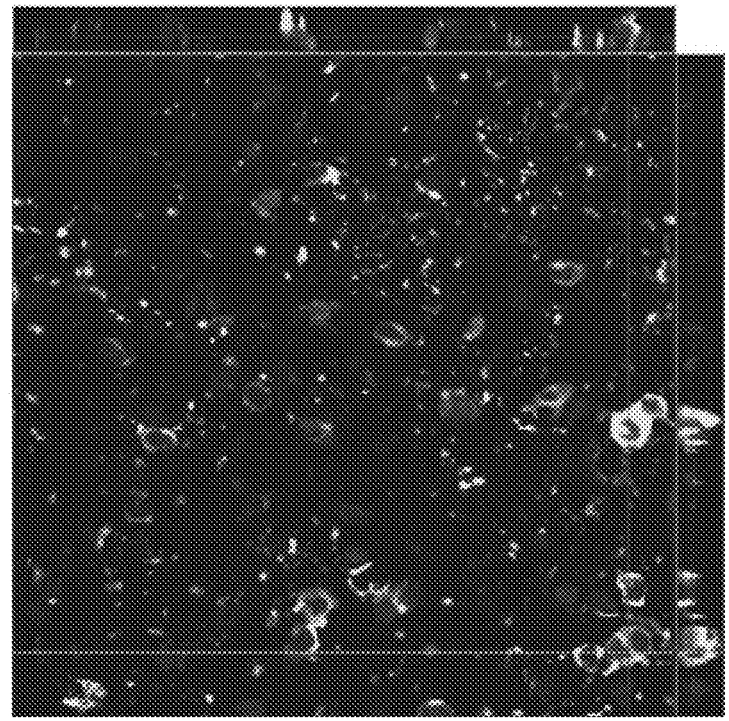
FIG. 10 is an image showing brain tissue sections stained for CNPase (green) and bisbenzimide (blue).
Figure 11:
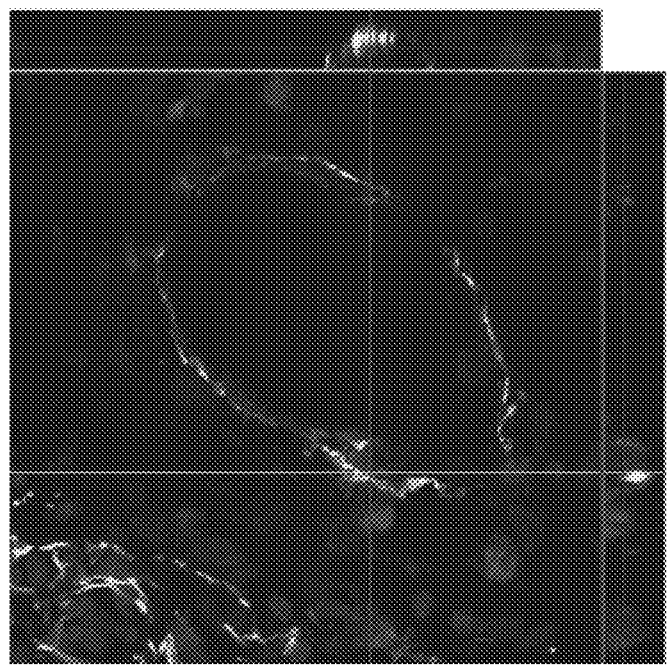
FIG. 11 is an image showing brain tissue sections stained for laminin (green) and bisbenzimide (blue).

To determine whether the hUCB treatment leads to angiogenesis, the brain slices from the hUCB treated and control rats were analyzed by double immunofluorescent staining. An immunofluorescent staining was conduced in the manner described above. The results indicate that several exogenous transplanted hUCB cells (bisbenzimide-labeled) showed vascular phenotypes (vWF+) around the perivascular and endothelial regions of the ischemic hemispheres of the treated rats (FIG. 7).

Cell migration along corticospinal tracts.

Figure 13A:
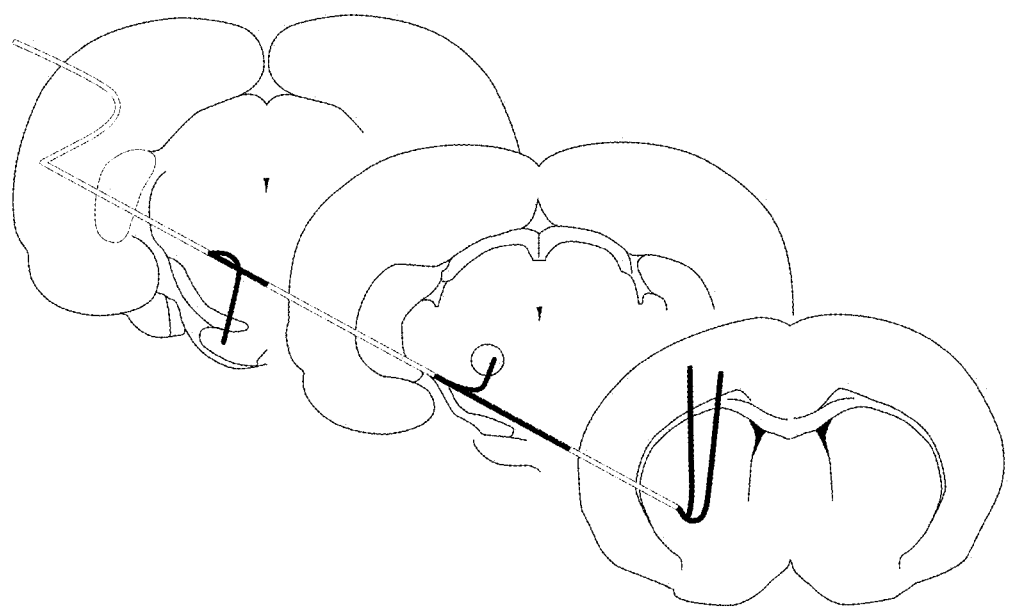
FIGS. 13A and B demonstrate a schematic and actual photomicrograph of the transportation of the injected dye along the regenerated corticospinal tract.
Figure 13B:

FIGS. 12 and 13 demonstrate the presence and movement of cells and/or injected dye along the regenerated corticospinal tract.

In summary, the results indicate that rats receiving hUCB cells intraparenchymally into the brain showed significantly improved neurological function following chronic cerebral ischemia in comparison with the control rats. In the hUCB treated group, exogenous transplanted stem cells were seen to migrate toward the cerebral infarcted zone and differentiate into glial cells (GFAP), neurons (Nestin$^+$, MAP-2$^+$ and Neu-N$^+$) and vascular endothelial cells (vWF$^+$), thereby enhancing neuroplasticty in the ischemic brain.

This invention is not limited in its application to the details of construction and the arrangement of components set forth in the foregoing description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having thus described several aspects of at least one embodiment of this invention, it is to be appreciated various alterations, modifications, and improvements will readily occur to those skilled in the art. Such alterations, modifications, and improvements are intended to be part of this disclosure, and are intended to be within the spirit and scope of the invention. Accordingly, the foregoing description and drawings are by way of example only.

What is claimed is:

1. A method for restoring control of muscular function in a subject with chronic stroke comprising:
intraparenchymally administering, to a brain of a human subject who has experienced a stroke, a therapeutically effective amount of an isolated umbilical cord blood cell population enriched in CD34$^+$, CD133$^+$, or CD34$^+$/CD133$^+$ cells,
wherein the isolated umbilical cord blood cell population is administered more than 7 days after the stroke.

2. The method of claim 1, wherein the isolated umbilical cord blood cell population is enriched in CD34+ umbilical cord blood cells.

3. The method of claim 1, wherein the isolated umbilical cord blood cell population is enriched in CD133+ umbilical cord blood cells.

4. The method of claim 1, wherein the isolated umbilical cord blood cell population is enriched in both CD34+/CD133+ umbilical cord blood cells.

5. The method of claim 1, wherein the isolated umbilical cord blood cell population comprises mononuclear cells that are at least 75% CD34+.

6. The method of claim 1, wherein the isolated umbilical cord blood cell population comprises mononuclear cells that are at least 90% CD34+.

7. The method of claim 1, wherein the isolated umbilical cord blood cell population comprises mononuclear cells that are at least 75% CD133+.

8. The method of claim 1, wherein the isolated umbilical cord blood cell population comprises mononuclear cells that are at least 90% CD133+.

9. The method of claim 1, wherein the isolated umbilical cord blood cell population comprises mononuclear cells that are at least 75% CD34+/CD133+.

10. The method of claim 1, wherein the isolated umbilical cord blood cell population comprises mononuclear cells that are at least 90% CD34+/CD133+.

11. The method of claim 1, wherein the subject is at least 60 years of age.

12. The method of claim 1, wherein at least $2\times10^6$ cells are administered to the subject.

13. The method of claim 1, wherein at least $5\times10^6$ cells are administered to the subject.

14. The method of claim 1, wherein at least $8\times10^6$ cells are administered to the subject.

15. The method of claim 1, wherein the isolated umbilical cord blood cell population is administered more than 1 month after the stroke.

16. The method of claim 1, wherein the isolated umbilical cord blood cell population is administered more than 6 months after the stroke.

17. The method of claim 1, wherein the isolated umbilical cord blood cell population is administered more than 1 year after the stroke.

18. The method of claim 1, wherein the isolated umbilical cord blood cell population is administered to three sites along a damaged cortical spinal tract.

19. The method of claim 1, wherein the isolated umbilical cord blood cell population is derived from a single cord blood unit.

20. The method of claim 1, wherein the isolated umbilical cord blood cell population is derived from multiple cord blood units.

21. The method of claim 1, wherein the isolated umbilical cord blood cell population shares less than 4 out of 6 histocompatibility markers with the subject.

22. The method of claim 1, wherein the isolated umbilical cord blood cell population shares at least 4 out of 6 histocompatibility markers with the subject.

23. A method for restoring control of muscular function in a subject with-brain tissue damage comprising:
intraparenchymally administering to a brain of a human subject who has experienced brain tissue damage a therapeutically effective amount of an isolated umbilical cord blood cell population enriched in CD34+, CD133+, or CD34+/CD133+ umbilical cord blood cells.

* * * * *